United States Patent
Abraham-Fuchs et al.

(10) Patent No.: US 8,551,424 B2
(45) Date of Patent: Oct. 8, 2013

(54) APPARATUS FOR PROCESSING A SAMPLE COMPRISING A BIOCHIP AND REAGENTS EMBEDDED IN A BIODEGRADABLE MATERIAL, AND PROCESSES THEREOF

(75) Inventors: Klaus Abraham-Fuchs, Erlangen (DE); Thomas Ehben, Weisendorf (DE); Walter Gumbrecht, Herzogenaurach (DE); Sebastian Schmidt, Erlangen (DE); Christian Zilch, Leipzig (DE)

(73) Assignee: Siemens Aktiengesellschaft, Munich (DE)

( * ) Notice: Subject to any disclaimer, the term of this patent is extended or adjusted under 35 U.S.C. 154(b) by 2089 days.

(21) Appl. No.: 11/594,938

(22) Filed: Nov. 9, 2006

(65) Prior Publication Data

US 2008/0182338 A1    Jul. 31, 2008

(30) Foreign Application Priority Data

Nov. 17, 2005  (DE) .......................... 10 2005 054 923

(51) Int. Cl.
*G01N 33/544* (2006.01)
*G01N 33/00* (2006.01)
*A61F 2/00* (2006.01)

(52) U.S. Cl.
USPC ........... 422/528; 422/529; 422/530; 422/129; 424/426

(58) Field of Classification Search
None
See application file for complete search history.

(56) References Cited

U.S. PATENT DOCUMENTS

| | | | |
|---|---|---|---|
| 5,459,078 A * | 10/1995 | Kline et al. | .................... 436/518 |
| 5,656,506 A * | 8/1997 | Kawaguchi et al. | .......... 436/534 |
| 6,403,038 B1 | 6/2002 | Heermann | |
| 2002/0150923 A1 | 10/2002 | Mailk | |
| 2003/0159944 A1 * | 8/2003 | Pottgen et al. | ............. 205/777.5 |
| 2004/0115094 A1 | 6/2004 | Gumbrecht et al. | |
| 2005/0152807 A1 | 7/2005 | Osterloh et al. | |

FOREIGN PATENT DOCUMENTS

| | | |
|---|---|---|
| DE | 197 30 497 C2 | 2/2000 |
| DE | 101 11 457 A1 | 9/2002 |
| DE | 103 54 806 A1 | 6/2005 |
| DE | 695 33 159 T2 | 7/2005 |
| DE | 10 2004 009 985 A1 | 9/2005 |
| WO | WO 01/35069 A1 | 5/2001 |
| WO | WO 02/16904 A2 | 2/2002 |

OTHER PUBLICATIONS

Park et al. "Fibroblast Activation Protein, a Dual Specificity Serine Protease Expressed in Reactive Human Tumor Stromal Fibroblasts". 1999. Journal of Biological Chemistry. vol. 275, No. 51, pp. 36505-36512.*
Kozlov, PV. "The structure and properties of solid gelatin and the principles of their modification". 1983. Polymer. vol. 24. pp. 651-666.*
German Office Action, Jun. 30, 2006.

* cited by examiner

*Primary Examiner* — Yelena G Gakh
(74) *Attorney, Agent, or Firm* — Harness, Dickey & Pierce, P.L.C.

(57) ABSTRACT

An apparatus is disclosed for processing a sample which stores processing reagents required for processing in a dry form. The processing reagents are covered by a biologically degradable medium or embedded in said biologically degradable medium.

50 Claims, 4 Drawing Sheets

APPARATUS FOR PROCESSING A SAMPLE COMPRISING A BIOCHIP AND REAGENTS EMBEDDED IN A BIODEGRADABLE MATERIAL, AND PROCESSES THEREOF

PRIORITY STATEMENT

The present application hereby claims priority under 35 U.S.C. §119 on German patent application number DE 10 2005 054 923.3 filed Nov. 17, 2005, the entire contents of which is hereby incorporated herein by reference.

FIELD

The present invention generally relates to an apparatus for processing a sample. For example, it may relate to one which stores processing reagents required for processing in a dry form, to a process for processing the sample and/or to a process for preparing the apparatus.

BACKGROUND

Biotechnology and genetic engineering have grown in importance in recent years. A basic problem is to detect biological molecules such as DNA (deoxyribonucleic acid) or RNA (ribonucleic acid), proteins, polypeptides, etc. Of great interest for many medical applications are in particular molecules which encode genetic information. Their detection in a sample of a patient enables, for example, pathogens to be detected, thereby facilitating a physician's diagnosis.

Appropriate analytical systems make increasingly use of "biochips" ("lab-on-a-chip systems") which can be used to detect biological molecules. Different types of biochips are known in which various measurement processes for detecting the molecules are employed. By using biochips, it is possible to construct compact, biological and medical analytical systems.

Embodiments are known in which the biochip is stored in a single-use unit (cartridge), and all steps, from sample processing to detection of the molecules, are carried out within said unit. The operation of such systems is inexpensive, since manual operations are mostly avoided. To carry out the analysis, the cartridge is usually introduced into a read-out and control instrument which controls the analytical process inside the cartridge and reads out measurement data.

For example, it is known that biological molecules can be detected by flushing the biochip with a liquid in which the molecules have been dissolved. This usually requires prior processing for extracting the molecules to be detected from the sample in order to avoid contaminations and facilitate detection. If DNA is to be detected, then it is usually additionally necessary to extract said DNA from cells or viruses present in the sample and amplify said DNA prior to the actual detection. This may be carried out, for example, by way of the "polymerase chain reaction (PCR)".

In known embodiments, the cartridge harbors a fluidic system which usually includes a plurality of microchannels. These microchannels can transport a liquid sample, for example a blood sample, from an input site to the biochip. In addition, it is possible to work up and process the sample in the channels or in reaction chambers in the cartridge which are connected to the microchannels.

Processing and analyzing the sample usually requires a plurality of different reagents, for example for dissolving the cells (lysis) and for PCR. In the case of compact, cartridge-based systems in particular, the question arises, how such processing reagents can be reacted with the sample. It is known that the required reagents can be transferred from reservoirs arranged in the read-out instrument to the fluidic system of the cartridge. It is moreover known to arrange appropriate reservoir chambers within the cartridge and to store the reagents there. In order to improve durability and storability of the cartridges, biochemical reagents, for example proteins and enzymes, in particular are stored in dry form. This has the additional advantage of it being possible to design a smaller cartridge than when storing liquid reagents.

Usually, reagents stored in dry form are soluble upon contact with water so that they can be reacted with the appropriately delivered sample. However, the fact that the dry reagents dissolve immediately upon contact with the sample or with water, starting the reaction, is not desired in every process step. It is in particular not desired if the sample needs to be washed in a chamber which contains dry reagents prior to the reaction in order to remove contaminations. This is necessary before carrying out a PCR, for example. The washing steps would reduce the concentration of already dissolved dry reagents at the site of the reaction to such an extent that a reaction can no longer take place. It is therefore desirable to dissolve the dry reagents only at a defined point during sample processing or analysis and to start the reaction.

DE-101 11 457 A1 describes a diagnostic device in which required reagents are stored as nonvolatile substances in a microfluidic system. Upon contact with water, the reagents dissolve and are thus available for a reaction or processing. The reagents may be kept ready, for example, in solid form or dissolved in a solid auxiliary substance, for example a water-soluble polymer.

It is known to cover dry reagents with a protective layer of paraffin. This firstly increases the half-life of the reagents and secondly, with the aid of the protective layer, enables the reagents to be released into the microfluidic circulation only at a point in time during the course of the measurement. This may be achieved, for example, by locally increasing the temperature, thereby melting the paraffin. However, the paraffin which now, in the molten state, is a droplet emulsion in the microfluidic circulation of the biochip may impair further processing steps or the analysis itself.

SUMMARY

In at least one embodiment of the present invention, an apparatus and/or a process is described for processing a sample, in which processing reagents required for processing are stored in a dry form, wherein said dry reagents can be released at a defined point in time, without interfering with subsequent work-up steps.

In at least one embodiment of the invention, an apparatus is provided in which processing reagents are present in dry form. Processing reagents include any types of reagents used for carrying out the analytical process. This may be, for example, reagents for cell disruption or PCR, and also reagents which facilitate hybridization of DNA fragments.

In at least one embodiment, the processing reagents are protected by a biologically degradable medium. For example, the processing reagents are at least partially surrounded by the biologically degradable medium. Biologically degradable media are intended to include any media, substances and agents which are degraded in a biochemical process by adding further media, substances, agents or microorganisms. It is possible, for example, to use enzymes for degradation. The same advantages as with covering the dry reagents by paraffin arise, namely improved half-life of the dry reagents compared to reagents not covered by a medium. An effect on subsequent reaction steps can however be avoided by degrading the medium. The degradation, for example, breaks up the medium into small units which do not influence the further course of the analysis.

According to at least one embodiment of the invention, the apparatus for processing the sample includes processing reagents in dry form. The processing reagents are embedded in the biologically degradable medium. In this way, the medium protects the processing reagents until the former is degraded and the latter can dissolve.

In an advantageous embodiment of the invention, the processing reagents and the medium form a nonhomogeneous mixture. This embodiment can be prepared particularly easily.

According to at least one embodiment of the invention, the apparatus for processing the sample includes processing reagents in dry form. The processing reagents are covered by the biologically degradable medium. This form of protection of the processing reagents is likewise readily preparable. More specifically, reactions between the substances used can essentially be avoided.

In an advantageous embodiment of the invention, the biologically degradable medium has a water-resistant design. The advantage here is the fact that the medium does not yet dissolve upon contact with water and thereby prevents the processing reagents stored underneath from dissolving. Thus the medium can be dissolved only by adding the degrading substance so that in an aqueous solution the processing reagents themselves are dissolved and thus react with the sample.

In a particularly advantageous embodiment of the apparatus, the medium includes at least one biopolymer. Here, a multiplicity of variations is available, which can be selected specifically for the corresponding applications of the analytical system. Moreover, biopolymers can readily be degraded by appropriate degrading reagents.

In an advantageous embodiment of the apparatus, the biopolymer is a protein. A multiplicity of conceivable embodiments of proteins, for example gelatin or collagen, is available, which can readily be degraded by corresponding enzymes. They may be present, for example, in a crosslinked form.

In a particularly advantageous embodiment of the apparatus, the biopolymer is a polysaccharide. Polysaccharides which may be used are, for example, dextran, starch or cellulose. These are particularly suitable for covering the reagents, since they can be prepared inexpensively and have a long half-life. Corresponding amylases for degradation are also available.

In another advantageous embodiment of the invention, the apparatus includes something for degrading the medium. This enables the processing reagents to be released without the need for supplying something for degrading the medium from the outside. Thus the apparatus can be operated essentially independently with regard to degradation of the medium and can have a compact design.

In a particularly advantageous embodiment of the invention, the apparatus comprises something for controlling the temperature of the elements/items for degrading the medium. The elements for degradation in this design have a temperature-dependent activity. This enables the degradation properties to be easily controlled as a function of the temperature so that degradation of the medium and thus delivery of the processing reagents to the sample can take place at a defined time.

Accordingly, in a particularly advantageous embodiment of the apparatus, the elements/items for degrading the medium are chosen so as for the medium to be degraded only above a defined temperature. Particularly advantageously, the elements for degrading the medium are in the form of HtrA2.

This temperature-dependent protease becomes active at temperatures of between 25° C. and 70° C. Another example is Pyrococcus furiosus alpha-amylase which displays a highly temperature-dependent activity between 40° C. and 120° C.

In a further advantageous embodiment of the invention, the elements/things for degrading the medium are designed as at least one degrading reagent stored in a dry form. This provides the same advantages as for the processing reagents stored in dry form. In this way, the half-life of the reagents and thereby the durability of the apparatus are increased.

In an advantageous embodiment of the invention, the medium is at least partially covered by the degrading reagent. This enables the apparatus to have a design which takes up as little space as possible, which is advantageous in particular in microfluidic systems. More specifically, a high concentration of the degrading reagent in the area of the medium to be degraded can be ensured when the former is dissolved.

Another embodiment of the invention is advantageous in that the degrading reagent is at least partially embedded in the medium. Thus, the degrading reagent is at least partially protected by the medium, even completely in a particularly advantageous manner.

In an advantageous embodiment of the invention, the apparatus includes at least one microchannel or one microcavity for receiving the processing reagents. The processing reagents and the degrading reagent are introduced as mixtures which form stable substances at room temperature.

In one particularly advantageous embodiment of the apparatus, the medium forms a protective layer for the processing reagents. In this way it is possible to achieve optimal protective action for the processing reagents.

The process according to at least one embodiment of the invention comprises:

providing a single-use analytical unit in which processing reagents required for processing are stored in a form stable at room temperature, the processing reagents being covered by a water-resistant, biologically degradable medium or being embedded in said medium, delivering the sample in an aqueous solvent, degrading the medium by using degrading reagents, dissolving the processing reagents in an aqueous solvent, and processing the sample by using the processing reagents.

This process can be carried out particularly easily and readily automated. In addition, the individual process steps can be adjusted to the special requirements of the particular analysis or processing.

BRIEF DESCRIPTION OF THE DRAWINGS

Further advantages of the invention are explained on the basis of the example embodiments described hereinbelow in conjunction with the accompanying drawings in which.

DETAILED DESCRIPTION OF THE EXAMPLE EMBODIMENTS

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

Figure 1:
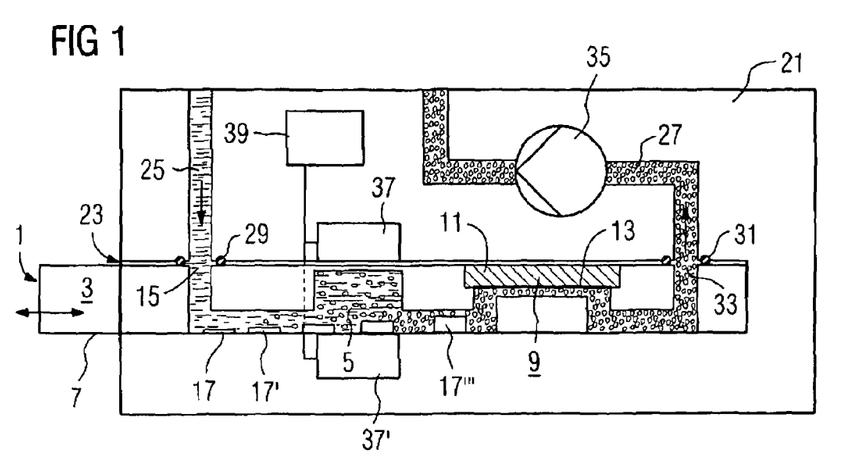
FIG. 1 depicts an analytical system including a cartridge and a read-out instrument.

FIG. 1 depicts a cartridge 1 which can be pushed into a receptacle 23 of a read-out instrument 21. In cartridge 1, an analysis of a sample can be carried out. The cartridge includes a plastic body 3 in which a microfluidic channel system 5 has been constructed. The plastic body 3 is covered by an adhesive film 7. This arrangement makes simple manufacturing of the cartridge 1 possible. Thus it is possible to mill the microfluidic channel system 5 into the plastic body 3 and subsequently sealing it by the adhesive film 7.

Cartridge 1 harbors a biochip 9 which may be constructed, for example, in the form of a silicon chip 11 having a sensitive area 13. Alongside the biochip 9 runs part of the microfluidic channel system 5 which, from an inlet 15, passes through a section in which reagents and auxiliary substances 17, 17', . . . , 17''' are arranged. A sample to be analyzed may be introduced via the inlet 15 into the microfluidic channel system 5. A chamber 19 in which the sample can be processed for analysis is located between the inlet 15 and the biochip 9. It is possible to arrange further chambers in the microfluidic channel system 5, if a plurality of processing steps are required.

The read-out instrument 21 includes fluidic channels 25 and 27, it being possible, for example, for water to be transported in the fluidic channel 21 from a solvent reservoir outside or inside the read-out instrument 21 via a seal 29 into the cartridge 1. Liquid is pumped by way of a pump 35 via a seal 31 of an outlet 33 to a waste container (inside or outside the read-out instrument 21) which is not depicted in FIG. 1.

Two heating elements 37 and 37' which can be used to control the temperature in the chamber 19 in a regulated manner are arranged in the read-out instrument 21. This is important, for example, for carrying out a PCR in the chamber 19. The two heating elements 37 and 37' are connected with a control unit 39 by which they are controlled.

Sample components present in the liquid may be processed in the cartridge. The sample may be, for example, a diluted or undiluted blood sample which is to be subjected, for example, to cell disruption by way of processing reagents. This releases DNA contained in the cells, which can be detected in a subsequent detection process for analyzing the sample. In this way it is possible to detect pathogens or gene mutations, for example.

Alternatively it is possible for the processing reagents to be suitable for carrying out copying of DNA fragments already present in the sample with appropriate thermocycling. In this case, the processing reagents contain appropriate substances used for PCR.

For the processing reagents, a multiplicity of other reagents are conceivable which can be applied to different processing or work-up steps, for example washing steps, hybridization or detections.

Figure 2:
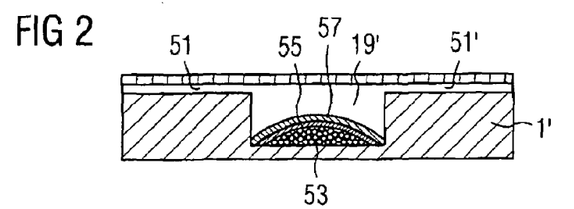
FIG. 2 is a cross section of a cartridge with a chamber in which a first solid is stored.

FIG. 2 depicts part of a cartridge 1' in the region of a chamber 19'. The cartridge 1' is similar to the cartridge 1 depicted in FIG. 1. In the chamber 19', for example, reactions with a sample can take place. There are microchannels of which a first channel 51 leads to the chamber 19' and a second channel 51' leads away from the chamber 19'. The chamber 19' may be sealed off by caps (not shown). There may be valves or the like which can be used to seal off the channels 51 and 51' at a suitable site.

The chamber 19' stores a first solid 53. The solid 53 is a reagent or a mixture of reagents, said mixture forming a storage-stable substance at room temperature. The solid 53 forms a layer on the bottom of the chamber 19'. The surface of the solid 53 is protected by a medium 55 which forms a thin film on the solid layer 53. As a result, the medium 55 forms a protective layer on the solid 53 so that the processing reagents are contacted with water or other solvents and thereby dissolved only at a defined point in time of the processing event. The medium is biologically degradable and not soluble in the solvent in which the solid 53 is to be dissolved. "Biologically degradable" is understood as meaning hereinbelow those media which can be degraded, i.e. divided into smaller units, within a biochemical reaction by microorganisms or biological substances. Usually, enzymes are used for degradation.

The medium 55 is covered by a degrading reagent 57 which is present in dry form and degrades the medium 55 only when dissolved. In the state of the cartridge 1', which is depicted in FIG. 2, all reagents are present in dry form and therefore no reaction or release takes place.

In one embodiment of the invention, processing reagents 53 protected in this way are provided inside the cartridge 1' by applying said processing reagents in a liquid form to at least one wall of the cartridge 1', for example by "spotting". The processing reagents are subsequently dried. The biologically degradable medium is provided in a soluble form, choosing an appropriate solvent in such a way that the processing reagents are not dissolved. Alternatively, the solvent may be chosen in such a rapidly drying form that the processing reagents are dissolved only to a small extent or not at all before drying. The medium dissolved in this way is applied to the processing reagents and subsequently dried. An example of a solvent which may be used is ether which dries relatively easily. Freeze-drying may be employed in order to accelerate the drying process.

Figure 3:
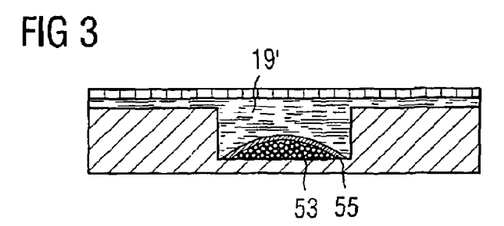
FIGS. 3 and 4 depict two functional steps of the device according to FIG. 2, FIGS. 5 and 6 are cross sections of another cartridge with a channel in which a solid is stored.

In FIG. 3, the chamber 19' is flooded with a solvent which may be, for example, a mixture of sample components and water. As a result, the degrading reagent 57 which in FIG. 2 was still in a solid form has dissolved. The degrading reagent 57 present in solution then degrades the protective medium 55, thus reducing the protective action.

Figure 4:
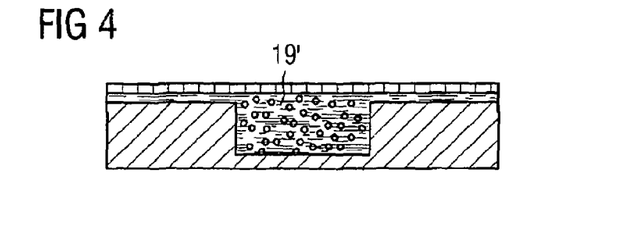

In FIG. 4, the protective layer has already been degraded completely and the solid 53 underneath has been dissolved by the solvent. The solid 53 has gone into solution or into suspension so that the dissolved reagent is present in the chamber 19' for further use purposes.

The medium used for forming the protective layer and the corresponding degrading reagent must be adjusted to one another. Likewise, it is important to choose suitable substances for the particular analytical process or processing event. It is particularly important here that the degradation products do not interfere with the process. The protective layer may consist, for example, of a biopolymer. Examples thereof are proteins or polysaccharides. Thus it is possible, for example, to use starch for the protective layer and amylase as the degrading reagent. Amylase which occurs inter alia in human saliva and in many bacteria is an enzyme which decomposes starch. Other examples of enzymatically degradable biopolymers are dextrans or gelatin which can be degraded by protease enzymes. Another conceivable protective material is cellulose, with cellulase being used as the degrading reagent. A reasonable purchasable example of a dextran is the inexpensive Chaetomium gracile Dextranase 3F.

A particular advantage is choosing the material of the protective layer and the degrading reagent in such a way that the protective layer is broken up into pieces as small as possible which do not interfere much with the further course of the measurement inside the apparatus.

It is advantageous if a reservoir with degrading reagents and a plurality of reservoirs with processing reagents and other work-up reagents, which in each case are protected by an appropriate protective layer, are arranged at various sites of the microfluidic channel system. It is possible, by distributing the degrading reagent dissolved, for example, in water in the microfluidic channel system, to degrade the protective layers of a plurality of reservoirs and to make accessible the processing reagents to the reaction. By flushing in water, the degrading reagents, for example in the form of enzymes, are distributed in the microfluidic system and dissolve the corresponding protective layers. Here the time until release of the processing reagents underneath the protective layer can be controlled via the thickness of the protective layer, the concentration of the degrading reagent and the temperature.

Figure 5:
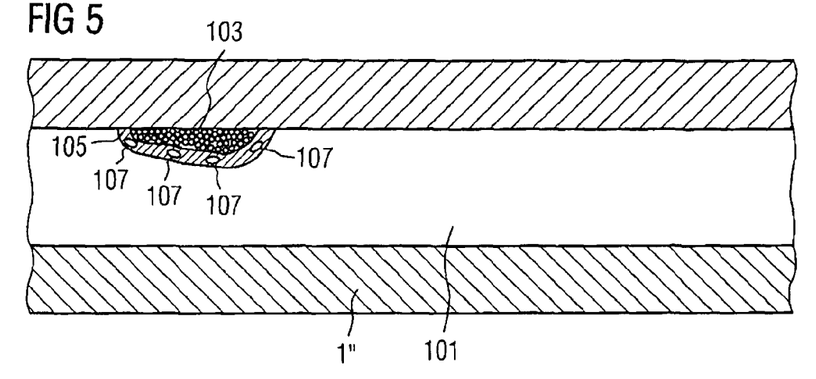

An alternative embodiment of the invention is depicted in FIG. 5. It depicts a section of a cartridge 1" which has a microfluidic channel 101. A reservoir of dry processing reagents 103 adheres to one wall of the microfluidic channel 101. The reagents are covered by a protective layer 105. Degrading reagents 107 are embedded in the protective layer 105 and are consequently likewise protected by the protective layer 105, which is advantageous in particular in the case of sensitive degrading reagents. The protective layer 105 is chosen so as to be modified when contacted with an appropriate solvent in such a way that the degrading reagents 107 are released. It consists, for example, of gelatin which swells upon contact with water. The degrading reagent 107 consists of a protease which can degrade gelatin. In the dry state, the protease is not active and the protective layer 105 is not degraded.

Figure 6:
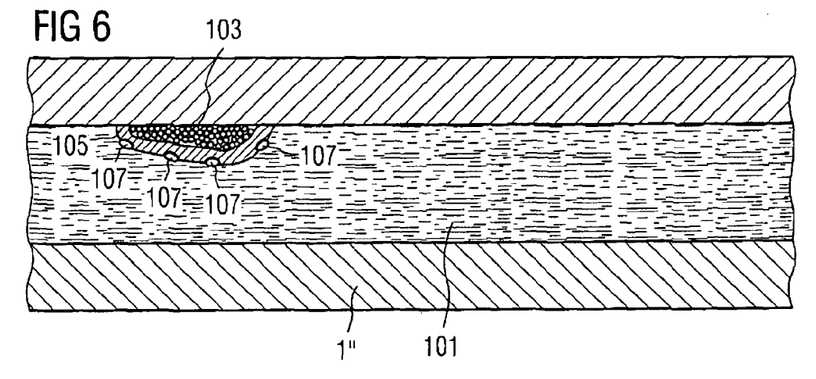

FIG. 6 depicts the same section of the cartridge 1" as FIG. 5. The microfluidic channel 101 is filled with water or an appropriate solvent so that the gelatin protective layer 105 is swollen. As a result, the degrading reagent 107 makes contact with said water and is dissolved. As soon as the degrading reagent 107 is in a soluble form, the protective layer 105 itself is degraded so that the processing reagents 103 can dissolve.

The mixed protective layer 105 with the processing reagents must be applied under suitable reaction conditions so that dissolving by the degrading reagent 107 does not take place with the reagents still being liquid. The degrading process should be started only upon swelling of the protective layer 105 after introducing water into the microfluidic channel 101. The reaction conditions may be adjusted, for example by adjusting the temperature or modifying the buffer composition so that the degrading reagent does not attack the protective layer while the reservoir is being prepared.

Figure 7:
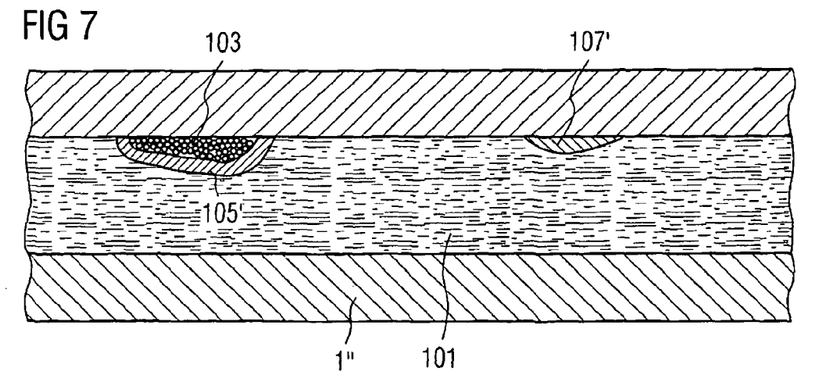
FIG. 7 depicts an alternative arrangement of the solid and a degrading reagent.

FIG. 7 depicts another embodiment of the invention. It depicts essentially the same section of the cartridge 1" as FIGS. 5 and 6. The processing reagents 103 are covered by a protective layer 105'. A reservoir containing degrading reagents 107' is stored at a different site of the microchannel 101. This site is located upstream of the processing reagents 103 as viewed in the direction of flow of the microfluidic channel 101. If water or an appropriate solvent is transported through the microfluidic channel 101, the degrading reagents 107' are dissolved and distributed in the microfluidic channel 101. They make contact with the biologically degradable protective layer 105', thereby degrading the protective layer 105'. This uncovers the processing reagents 103 which, as a result, for their part are dissolved in the solvent.

In the example embodiments demonstrated above, the degrading reagent is dissolved due to contact with water or an appropriate solvent. The dissolved degrading reagent degrades the protective layer of the processing reagents and the latter dissolve. However, immediate degradation of the protective layer upon contact with the degrading reagents is not desirable in all analytical processes. Thus some process steps require the sample to be washed beforehand. However, the processing reagents are intended to react with the sample only after the washing process. This problem is addressed in the following example embodiment.

Figure 8:
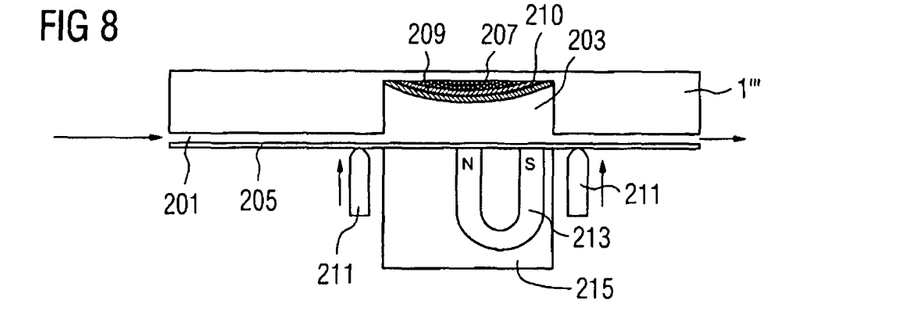
FIG. 8 is a cross section of a further cartridge with a chamber in which a first solid is stored.

FIG. 8 depicts a section of a cartridge 1'''. The cartridge 1''' includes a microfluidic channel 201 and a chamber 203. Microfluidic channel 201 and the chamber 203 are covered by an adhesive film 205. The chamber 203 stores reagents 207 which are covered by a protective layer 209. The reagents 207 are water-soluble and the protective layer 209 is biologically degradable. The protective layer 209 is covered with a dry degrading reagent 210. Two valves 211 and one magnetic unit 213 each of which are depicted here only with symbols are arranged underneath the adhesive film 205. The magnetic unit 213 is integrated in a temperature unit 215 by means of which the temperature inside the chamber 203 can be controlled in a regulated manner. The valves 211, the magnetic unit 213 and the temperature unit 215 are arranged, for example, in the read-out instrument which is not depicted here.

Figure 9:
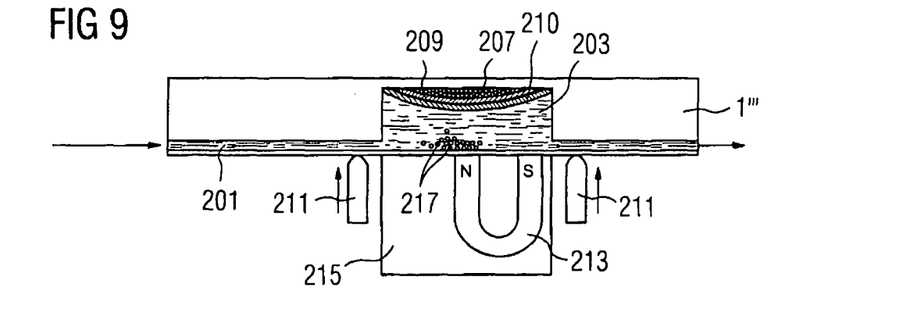
FIGS. 9 to 11 depict three functional steps of the cartridge according to FIG. 8.

FIG. 9 depicts the way in which liquid is introduced through the microfluidic channel 201 into the chamber 203. The liquid flows through the chamber 203 and follows the further course of the microfluidic channel 201. The liquid contains components of the sample to be analyzed, for example DNA fragments, which have been obtained in processing steps carried out previously. These components are coupled to "magnetic beads" 217 which, when flowing through the chamber 203, are arrested by the magnetic field of the magnetic unit 213. The components of the sample are washed and contaminations are removed from the chamber 203 by water flowing through afterwards for a defined period of time.

At the same time, however, the degrading reagent also dissolves due to contact with the water. At this point in the process, it would be disadvantageous if the degrading reagent 210 would degrade the protective layer 209, since in this case parts of the reagents 207 would also be flushed out. In order to avoid premature degradation of the protective layer 209, the degrading reagent 210 used may be, for example, a temperature-dependent protease which may be in the form of HtrA2, for example, which becomes active at temperatures of between 25° C. and 70° C. Another example is Pyrococcus furiosus alpha-amylase which displays a highly temperature-dependent activity between 40° C. and 120° C. It is thus possible to ensure that the protective layer is degraded only upon a temperature increase by the temperature unit 215.

As an alternative, it is also possible to employ proteases whose activity is highly buffer-dependent, such as, for example, calcium ion-, zinc ion-, pH- or ATP-dependent proteases. Thus, the enzyme may be carboxypeptidase, for example, which becomes active only in the presence of appropriate metal ions such as zinc or calcium. Such an enzyme can be activated by adding a buffer solution containing appropriate metal ions. pH-activated enzymes are likewise known. Thus, for example, pepsin becomes active only at a low pH, about 1.8. The activation here is by way of autocatalysis. Pepsin is inactive at a higher buffer pH. The activity of the enzyme can consequently be controlled in a simple manner by adding an appropriate buffer.

Alternatively, it is possible that the degrading reagent is not kept in a reservoir inside the microfluidic system but is introduced on a storage container or already premixed with the sample into the microfluidic system before or during the processing event.

Figure 10:
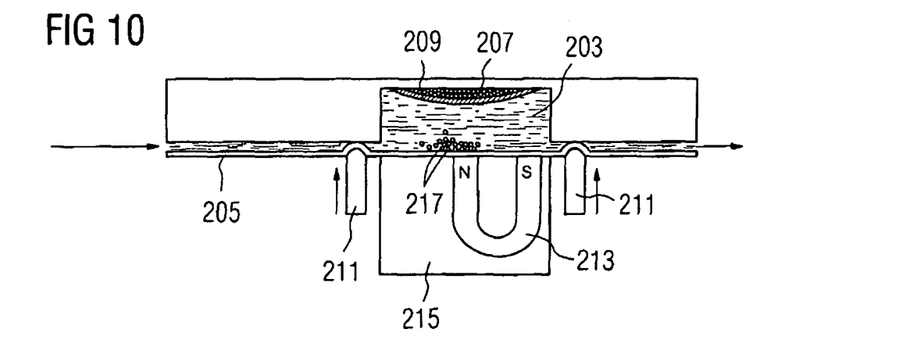

Care should be taken that a sufficient amount of the degrading reagent 210 is present so that there is still enough thereof after the washing in order to degrade the protective layer 209. After the washing the valves 211 may be closed as depicted in FIG. 10. For this purpose, the valves 211 push the adhesive film 205 upwards so that the chamber 203 is closed. The degrading reagent 210 is present in a soluble form.

Figure 11:
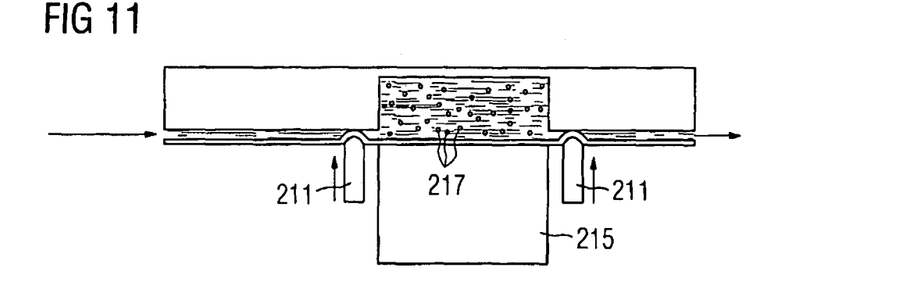

FIG. 11 depicts the arrangement after specifically increasing the temperature by means of the temperature unit 215. Due to the increase in temperature, the degrading reagent 210 present in the solution has degraded the protective layer 209. As a result, the reagents 207 were exposed to the aqueous solvent and are now likewise present in solution. The magnetic field of the magnetic field unit 213 was switched off so that the magnetic beads 217 have been distributed in the solution. Therefore, the reaction between the sample components and the reagents can take place.

The embodiment described is particularly advantageous when carrying out a PCR. Here it is desirable for the DNA to be copied to be in a purified form, if possible, so that the PCR run is not impaired. The temperature unit 215 may be used for carrying out the temperature cycles necessary for PCR, with the reagents 207 necessary for PCR being dissolved automatically during the first cycle.

Figure 12:
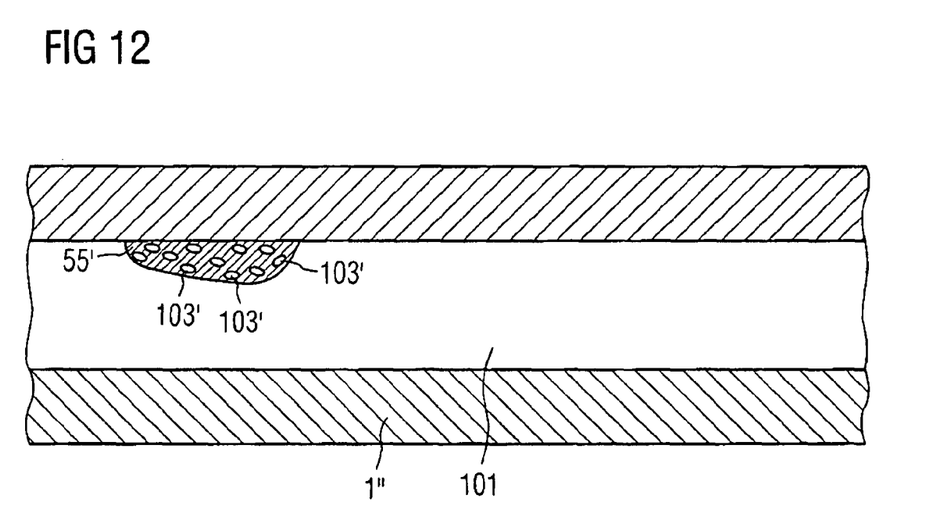
FIG. 12 is a cross section of a another cartridge with a channel in which processing reagents are stored.

An alternative embodiment of the invention is depicted in FIG. 12 which, in analogy to FIGS. 5 to 7, depicts a cartridge 1". In the cartridge 1", a microfluidic channel 101 has been formed. In contrast to the embodiments depicted in FIGS. 5 to 7, the processing reagents 103' are embedded in a biologically degradable medium 55, in which they are present as inclusions. As soon as an appropriate solvent containing degrading reagents for the medium 55, reaches the microfluidic channel 101, the medium 55, begins to decompose. As a result, the processing reagents 103' protected by the medium 55' are gradually released and dissolve. A sample which has likewise been delivered is processed by the processing reagents 103', i.e. is subjected to cell disruption, for example.

The processing reagents 103' depicted in FIG. 12 and embedded in the medium 55, are prepared, for example, by providing a mixture of the medium 55, with the processing reagents 103' in a liquid form and providing the cartridge 1". The liquid mixture is applied to one wall of the cartridge 1" and finally dried. This produces, in the case of a nonhomogeneous mixture, the inclusions of the processing reagents 103' in the medium 55. Alternatively, the substances may also form a homogeneous mixture. When choosing the processing reagents 103' and the medium 55', care should be taken that the two substances do not react with one another. Drying may be carried out by way of freeze-drying, for example.

By using the degradable protective layer above the dry reagents, it is possible to use protective layers which do not adversely influence the later course of analyzing the sample. This reduces the number of failures of such analytical processes while increasing the accuracy and quality of measurement at the same time.

Alternatively, it is conceivable to add such elements/things for degrading the medium to the sample even before introduction into the apparatus.

Further, elements and/or features of different example embodiments may be combined with each other and/or substituted for each other within the scope of this disclosure and appended claims.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An apparatus for processing a sample, comprising:
    a cartridge having at least one microfluidic channel formed therein;
    a biochip; and
    processing reagents in dry form stored in the cartridge, wherein the processing reagents are embedded in a biologically degradable medium which is not soluble in its non-degraded state in a solvent in which the reagents are dissolved.

2. The apparatus as claimed in claim 1, wherein the processing reagents and the biologically degradable medium form a nonhomogeneous mixture.

3. The apparatus as claimed in claim 1, wherein the processing reagents are present as inclusions inside the degradable medium.

4. The apparatus as claimed in claim 1, wherein the medium comprises at least one biopolymer layer covering an outer surface of the processing reagents.

5. The apparatus as claimed in claim 4, wherein the biopolymer is a protein.

6. The apparatus as claimed in claim 5, wherein the protein is gelatin.

7. The apparatus as claimed in claim 4, wherein the biopolymer is a polysaccharide.

8. The apparatus as claimed in claim 7, wherein the polysaccharide is a dextran.

9. The apparatus as claimed in claim 7, wherein the polysaccharide is starch.

10. The apparatus as claimed in claim 7, wherein the polysaccharide is cellulose.

11. The apparatus as claimed in claim 1, further comprising means for degrading the medium.

12. The apparatus as claimed in claim 11, wherein the means for degrading the medium include at least one enzyme.

13. The apparatus as claimed in claim 11, further comprising:
    means for controlling the temperature of the means for degrading the medium, said means for degrading including a temperature-dependent activity.

14. The apparatus as claimed in claim 13, wherein the means for degrading the medium are chosen so as for the medium to be degraded only above a defined temperature.

15. The apparatus as claimed in claim 11, wherein the means for degrading the medium comprise HtrA2.

16. The apparatus as claimed in claim 11, wherein the means for degrading the medium comprise Pyrococcus furiosus alpha-amylase.

17. The apparatus as claimed in claim 11, wherein the means for degrading the medium have a pH-dependent activity.

18. The apparatus as claimed in claim 11, wherein the means for degrading the medium have an ion-dependent activity.

19. The apparatus as claimed in claim 11, wherein the means for degrading the medium are designed as at least one degrading reagent stored in a dry form.

20. The apparatus as claimed in claim 19, wherein the medium is at least partially covered by the degrading reagent.

21. The apparatus as claimed in claim 19, wherein the degrading reagent is at least partially embedded in the medium.

22. The apparatus as claimed in claim 19, wherein the degrading reagent is activatable by contacting the medium with water.

23. The apparatus as claimed in claim 19, wherein the degrading reagent is water-soluble.

24. The apparatus as claimed in claim 1, further comprising:
at least one microchannel or one microcavity for receiving the processing reagents, into which said processing reagents and the degrading reagent have been introduced as mixtures which form stable substances at room temperature.

25. The apparatus as claimed in claim 24, wherein the mixtures are anhydrous solids.

26. The apparatus as claimed in claim 24, wherein at least one of the solids adheres to walls of the microchannel or of the microcavity.

27. An apparatus for processing a sample, comprising:
a cartridge having at least one microfluidic channel formed therein;
a biochip; and
processing reagents in dry form stored in the cartridge, wherein the processing reagents covered by a biologically degradable medium which is not soluble in its non-degraded state in solvent in which the reagents are dissolved.

28. The apparatus as claimed in claim 27, wherein the medium forms a protective layer for the processing reagents.

29. The apparatus as claimed in claim 27, wherein the medium is water-resistant in its non-degraded state.

30. The apparatus as claimed in claim 27, wherein the medium comprises at least one biopolymer.

31. The apparatus as claimed in claim 27, further comprising means for degrading the medium fixed to the at least one microchannel and one microcavity.

32. The apparatus as claimed in claim 31, wherein the means for degrading the medium include at least one enzyme.

33. The apparatus as claimed in claim 31, further comprising:
means for controlling the temperature of the means for degrading the medium, said means for degrading including a temperature-dependent activity.

34. The apparatus as claimed in claim 27, further comprising:
at least one microchannel or one microcavity for receiving the processing reagents, into which said processing reagents and the degrading reagent have been introduced as mixtures which form stable substances at room temperature.

35. A process for processing a sample, comprising:
providing an apparatus for processing a sample, including processing reagents required for processing the sample, stored in a dry form, and a biologically degradable medium that is not soluble in a non-degraded state in a solvent in which the reagents are dissolved, the processing reagents being at least one of covered by and embedded in the biologically degradable medium;
delivering the sample in an aqueous solvent;
degrading the medium by using degrading reagents;
dissolving the processing reagents in the aqueous solvent; and
processing the sample by using the processing reagents.

36. The process as claimed in claim 35, wherein the apparatus contains a reservoir of the processing reagent.

37. The process as claimed in claim 35, wherein the degrading reagent is delivered with the sample.

38. The process as claimed in claim 35, wherein the temperature of the degrading reagent is increased so as for the medium to be degraded.

39. A process for preparing an apparatus for processing a sample, including processing reagents required for processing the sample, stored in a dry form, and a biologically degradable medium that is not soluble in a non-degraded state in a solvent in which the reagents are dissolved, the processing reagents being at least one of covered by and embedded in the biologically degradable medium, the process comprising:
providing a mixture including at least the processing reagents;
at least one of covering and embedding the reagents in the biologically degradable medium;
providing a reaction vessel;
applying the mixture to at least one wall of the reaction vessel; drying the mixture; and
providing a degrading reagent layer on at least one of the biologically degradable medium and on the wall of the reaction vessel.

40. The process as claimed in claim 39, further comprising applying the mixture to the wall by spotting.

41. A process for preparing an apparatus for processing a sample, including processing reagents required for processing the sample, stored in a dry form, and a biologically degradable medium, water-resistant in a non-degraded state, the processing reagents being at least one of covered by and embedded in the biologically degradable medium, the process comprising:
providing a reaction vessel;
applying the processing reagents to at least one wall of the reaction vessel;
drying the processing reagents;
providing the biologically degradable medium in soluble form;
solublizing the medium using in a solvent that does not dissolve the processing reagents;
applying the dissolved medium to the processing reagents;
drying the dissolved medium; and
covering the biologically degradable medium with a degrading reagent layer.

42. The process as claimed in claim 41, wherein the solvent is ether.

43. The process as claimed in claim 42, wherein drying is carried out by way of freeze-drying.

44. An apparatus for processing a sample, comprising:

processing reagents required for processing the sample, stored in a dry form in the apparatus; and a biologically degradable medium that is not soluble in a non-degraded state in a solvent in which the reagents are dissolved, the processing reagents being at least one of covered by and embedded in the biologically degradable medium.

45. The apparatus as claimed in claim 44, wherein the processing reagents and the biologically degradable medium form a nonhomogeneous mixture.

46. The apparatus as claimed in claim 44, wherein the processing reagents are present as inclusions inside the degradable medium.

47. The apparatus as claimed in claim 44, further comprising means for degrading the medium covering the degradable medium.

48. The apparatus as claimed in claim 47, wherein the means for degrading the medium include at least one enzyme.

49. The apparatus as claimed in claim 47, further comprising:

means for controlling the temperature of the means for degrading the medium, said means for degrading including a temperature-dependent activity.

50. The apparatus as claimed in claim 44, further comprising:

at least one microchannel and one microcavity for receiving the processing reagents, into which said processing reagents and the degrading reagent have been introduced as mixtures which form stable substances at room temperature.

* * * * *